United States Patent
Tribus (10) Patent No.: US 9,439,691 B2
(45) Date of Patent: Sep. 13, 2016

(54) FIXATION-BASED SURGERY

(76) Inventor: Clifford Tribus, Madison, WI (US)

( * ) Notice: Subject to any disclaimer, the term of this patent is extended or adjusted under 35 U.S.C. 154(b) by 765 days.

(21) Appl. No.: 12/785,026

(22) Filed: May 21, 2010

(65) Prior Publication Data
US 2010/0298885 A1    Nov. 25, 2010

Related U.S. Application Data

(60) Provisional application No. 61/180,625, filed on May 22, 2009.

(51) Int. Cl.
*A61B 17/70*    (2006.01)

(52) U.S. Cl.
CPC ........ *A61B 17/7077* (2013.01); *A61B 17/7001* (2013.01)

(58) Field of Classification Search
CPC .......... A61B 17/7074; A61B 17/7077; A61B 17/7079; A61B 17/708; A61B 17/0293; A61B 17/025; A61B 17/0206; A61B 19/26; A61B 2017/0256; A61B 2019/268
USPC ....... 600/193, 196, 197, 213, 214, 215, 216, 600/219, 226, 227, 228, 229, 230, 234, 600/238; 606/104, 86 A, 246, 279
See application file for complete search history.

(56) References Cited

U.S. PATENT DOCUMENTS

| | | | |
|---|---|---|---|
| 3,040,739 A * | 6/1962 | Grieshaber | 600/228 |
| 3,941,365 A | 3/1976 | Frymoyer | |
| 4,733,657 A | 3/1988 | Kluger | |
| 4,863,133 A * | 9/1989 | Bonnell | 248/280.11 |
| 4,926,849 A * | 5/1990 | Downey | 602/34 |
| 5,239,716 A | 8/1993 | Fisk | |
| 5,478,340 A * | 12/1995 | Kluger | 606/86 A |
| 5,728,046 A * | 3/1998 | Mayer et al. | 600/210 |
| 5,891,157 A | 4/1999 | Day et al. | |
| 6,755,828 B2 * | 6/2004 | Shevtsov | A61B 17/8625 606/246 |
| 7,166,113 B2 | 1/2007 | Arambula et al. | |
| 7,655,008 B2 * | 2/2010 | Lenke | A61B 17/025 606/246 |
| 7,794,464 B2 * | 9/2010 | Bridwell | A61B 17/025 606/265 |
| 7,918,878 B2 * | 4/2011 | Songer | A61B 17/7002 606/279 |
| 8,221,426 B2 * | 7/2012 | Justis | A61B 17/708 606/86 A |
| 8,551,141 B2 * | 10/2013 | Gephart | A61B 17/3421 606/246 |
| 8,821,502 B2 * | 9/2014 | Gleeson | A61B 17/708 606/105 |
| 8,951,257 B2 * | 2/2015 | Lenke | A61B 17/708 606/86 A |
| 9,211,145 B2 * | 12/2015 | Pereiro De Lamo | A61B 17/7032 |
| 2005/0033291 A1 | 2/2005 | Ebara | |
| 2005/0216026 A1 * | 9/2005 | Culbert | 606/96 |
| 2006/0025778 A1 | 2/2006 | Ferree | |
| 2006/0036245 A1 | 2/2006 | Stern | |
| 2006/0036273 A1 | 2/2006 | Siegal | |
| 2006/0149236 A1 | 7/2006 | Barry | |
| 2006/0271050 A1 * | 11/2006 | Piza Vallespir | 606/61 |

(Continued)

FOREIGN PATENT DOCUMENTS

DE    ep0602351 a1 *    6/1994

*Primary Examiner* — Lynnsy Summitt
(74) *Attorney, Agent, or Firm* — Foley & Lardner LLP (57) ABSTRACT

A stabilization system includes one or more leverage members configured to be mounted to a vertebra. The one or more leverage members are further configured to allow a user to manipulate the vertebra to a desired position. The stabilization system also includes a mounting bracket configured to mount to the one or more leverage members such that the one or more leverage members are immobilized. The mounting bracket is mounted to a support.

20 Claims, 8 Drawing Sheets

(56) References Cited

U.S. PATENT DOCUMENTS

| | | |
|---|---|---|
| 2007/0016188 A1 | 1/2007 | Boehm, Jr. et al. |
| 2007/0016199 A1 | 1/2007 | Boehm, Jr. et al. |
| 2007/0083210 A1 | 4/2007 | Hestad et al. |
| 2007/0118119 A1 | 5/2007 | Hestad |
| 2007/0123989 A1 | 5/2007 | Gfeller et al. |
| 2007/0156157 A1 | 7/2007 | Nahum et al. |
| 2007/0213715 A1* | 9/2007 | Bridwell et al. ............... 606/61 |
| 2008/0021284 A1 | 1/2008 | Hestad et al. |
| 2008/0294206 A1* | 11/2008 | Choi et al. ............... 606/86 A |
| 2011/0172714 A1* | 7/2011 | Boachie-Adjei ... A61B 17/7086 606/264 |

* cited by examiner

FIXATION-BASED SURGERY

CROSS-REFERENCE TO RELATED APPLICATIONS

This application claims priority to U.S. Provisional Patent Application No. 61/180,625, filed May 22, 2009, which is incorporated by reference in its entirety.

FIELD

The subject matter of the disclosure relates generally to the correction and stabilization of vertebral bodies in the spinal column. More specifically, the subject matter of the disclosure relates to a fixation-based surgical system and method for improving surgical efficiency and results.

BACKGROUND

A human spinal column provides support for the body and protection for the delicate spinal cord and nerves. The spinal column includes a series of vertebrae stacked on top of each other. Each vertebra has a vertebral body located in an anterior portion of the spinal column. The vertebral bodies provide a majority of the weight-bearing support for the spinal column. Situated between each vertebral body is an intervertebral disc, which provides cushioning and dampening of compressive forces applied to the spinal column. Located posterior to the vertebral body and intervertebral disc is the spinal canal, which contains the spinal cord and nerves. Posterior to the spinal canal are the articulating processes of the vertebrae.

Various types of spinal column disorders are known. These spinal column disorders include scoliosis (abnormal lateral curvature of the spine), spondylolisthesis (forward displacement of one vertebra over another, usually in a lumbar or cervical spine), kyphosis (exaggerated round back), post traumatic deformity, and other disorders caused by abnormalities, disease, or trauma, such as ruptured or slipped discs, degenerative disc disease, fractured vertebra, tumors, and the like. Patients that suffer from such conditions often experience extreme and debilitating pain. Many patients with spinal column disorders also suffer from neurologic deficit. For some patients, spinal column disorders can be at least partially treated through spinal surgery.

DETAILED DESCRIPTION

To help correct scoliosis, spondylolisthesis, and other spinal disorders, surgeons often have to manipulate a plurality of vertebrae to desired positions. Once the plurality of vertebrae are in the desired positions, a stabilizing rod can be mounted to at least the plurality of vertebrae to hold the vertebrae in place. The inventor has perceived that traditional vertebral manipulation can be overly strenuous on the patient, and may require multiple individuals to hold individual vertebra in place as the surgeon makes additional adjustments. For example, the surgeon may manipulate a first vertebra to a desired position using a leverage member mounted to the first vertebra. A surgical assistant (i.e., another doctor or surgeon, a nurse, etc.) may hold the first vertebra in place while the surgeon manipulates a second vertebra to a desired position using a leverage member mounted to the second vertebra. The same or a different surgical assistant may hold the second vertebra in place while the surgeon manipulates a third vertebra, and so on. As such, numerous surgical assistants may be required to assist the surgeon in holding the vertebrae, resulting in additional cost to perform the surgery. Also, if a surgical assistant allows a positioned vertebra to move, the surgeon may have to re-position the vertebra, resulting in extra strain on the patient. Further, the patient may be further harmed if the surgical assistant places too much pressure on a positioned vertebra.

As such, the inventor has perceived a fixation-based surgical system for use during surgery. The fixation-based surgical system can include a fixed structure which the surgeon can use to hold manipulated vertebrae in place as additional vertebrae are manipulated. The fixation-based surgical system can also be used by the surgeon to manipulate the vertebrae. As an example, it may be determined that three vertebrae are to be manipulated in order to correct a spinal deformation. The surgeon can attach one or more leverage members to the first vertebra, manipulate the first vertebra to a desired position, and secure the one or more leverage members to the fixation-based surgical system. The surgeon can repeat the process for the second vertebra and for the third vertebra. When all of the vertebrae have been manipulated by the surgeon, the surgeon can secure a stabilizing rod to the spinal column to hold all of the vertebrae in place. Once secured to the stabilizing rod, the surgeon can release the vertebrae from the fixation-based surgical system, remove the one or more leverage members from each vertebra, and complete the operation. As such, the surgery can be performed by a single surgeon in a cost-effective manner without placing unnecessary strain on the patient.

In one embodiment, the leverage members can extend from screws inserted to vertebrae. The leverage members can be attached to a rigid, fixed point in space (i.e., the operating table, a wall, a ceiling, a floor, etc.). In one embodiment, the leverage members may be secured to the rigid, fixed point using brackets. The brackets may include holes, c-rings with clamps, ratchets, thumb screws, etc. Alternatively, any other type of bracket and/or method of securing the leverage members may be used. The leverage members can be manipulated in space, relative to the fixed point and to one another. In one embodiment, the leverage members can have at least 6 degrees of freedom of movement. These degrees of freedom can include movement in the medial direction, movement in the lateral direction, movement in the ventral direction, movement in the dorsal direction, and two-way rotation about any axis which runs through a vertebra. Alternatively, fewer, additional, and/or different degrees of freedom of movement may be used. Once an entire deformity is corrected and fixed in space relative to the rigid, fixed point, one or more of the stabilizing rods can be attached to the vertebrae to stabilize the correction by linking each vertebral body to an adjacent vertebral body. Upon stabilization with the stabilization rods, the leverage members may be released from the rigid, fixed point and/or from the vertebrae.

Figure 1:
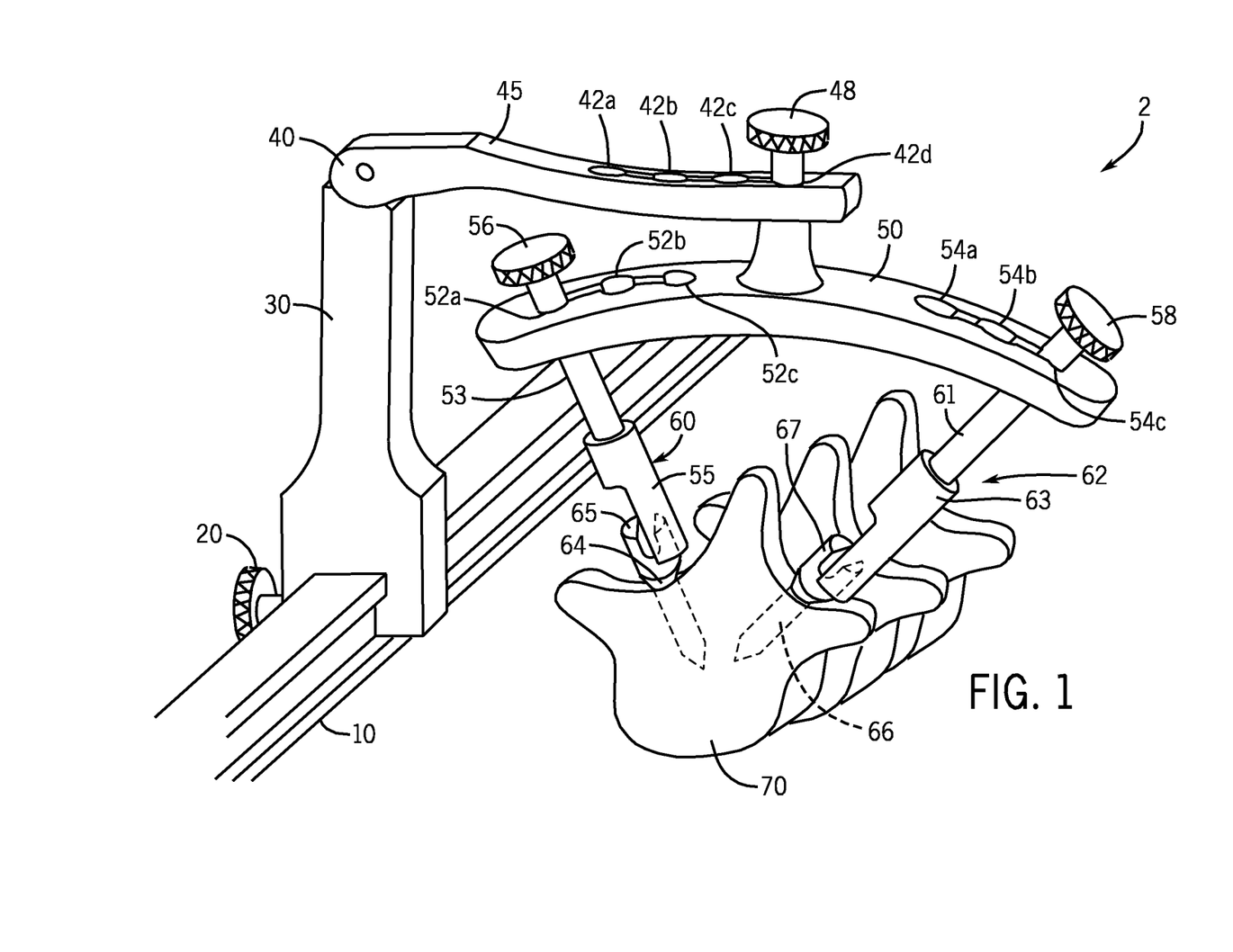
FIG. 1 is a perspective view of a fixation-based surgical system in accordance with an illustrative embodiment.

FIG. 1 is a perspective view of a fixation-based surgical system 2 in accordance with an illustrative embodiment. Fixation-based surgical system 2 can be used by a surgeon to manipulate one or more vertebrae of a spinal column and/or to secure one or more manipulated vertebrae of the spinal column during spinal surgery. As such, additional vertebra(e) can be manipulated without moving or adversely effecting the already manipulated vertebra(e). Fixation-based surgical system 2 includes a rail 10, an upright 30, an arm 45, and a mounting bracket 50. In alternative embodiments, fixation-based surgical system 2 may include additional, fewer, and/or different components.

As illustrated with reference to FIG. 1, fixation-based surgical system 2 is mounted to a vertebra 70 of a spinal column of a patient. A surgeon (or other user) can access vertebra 70 using surgical techniques known to those of skill in the art. Once accessed, the surgeon can mount a first fixation member 64 to a first portion of vertebra 70, and a second fixation member 66 to a second portion of vertebra 70. In alternative embodiments, additional or fewer fixation members may be used. For example, in one embodiment, four fixation members may be mounted to each vertebra that is to be manipulated. In an illustrative embodiment, first fixation member 64 and second fixation member 66 can be poly-axial bone screws or any other type of bone screws as known to those of skill in the art. Alternatively, anchors, dowels, and/or any other type of fixation member may be used. In one embodiment, first fixation member 64 and second fixation member 66 can have a length between 20 and 80 millimeters, inclusive. Alternatively, any other length may be used.

First fixation member 64 includes a first mounting portion 65 that extends from vertebra 70, and second fixation member 66 includes a second mounting portion 67 that extends from vertebra 70. Depending on the embodiment, first mounting portion 65 and second mounting portion 67 may be permanently or detachably mounted to the respective bone screw (or other) portions of first fixation member 64 and second fixation member 66. As illustrated in FIG. 1, a first leverage member 60 can be mounted to first mounting portion 65 of first fixation member 64, and a second leverage member 62 can be mounted to second mounting portion 67 of second fixation member 66. In one embodiment, first mounting portion 65 and second mounting portion 67 can be threaded stems configured to mate with first leverage member 60 and second leverage member 62, respectively. Alternatively, any other mounting configuration such as mating connectors, bolts, screws, etc. may be used. In another alternative embodiment, first leverage member 60 and second leverage member 62 may be permanently mounted to first fixation member 64 and second fixation member 66, respectively.

First leverage member 60 and second leverage member 62 can each be adjustably mounted to mounting bracket 50. For example, first leverage member 60 can be secured to a mounting hole 52a, a mounting hole 52b, or a mounting hole 52c. Similarly, second leverage member 62 can be secured to a mounting hole 54a, a mounting hole 54b, or a mounting hole 54c. First leverage member 60 includes a threaded rod 53 and a base 55 configured to mate with threaded rod 53. Base 55 is also configured to be secured to first mounting portion 65 of first fixation member 64. As such, a leverage member adjuster 56 can be used to turn threaded rod 53 and manipulate vertebra 70 in a direction which is substantially perpendicular to a top surface of a surgical table (not shown). As used herein, substantially parallel and substantially perpendicular can refer to an orientation which is within forty-five degrees of being precisely parallel or precisely perpendicular, respectively. Similarly, second leverage member 62 can include a threaded rod 61 and a base 63 configured to mate with threaded rod 61. Base 63 can also be configured to be secured to second mounting portion 67 of second fixation member 66. A leverage member adjuster 58 can be used to turn threaded rod 61 and manipulate vertebra 70 in the direction which is substantially perpendicular to the top surface of the surgical table. In an alternative embodiment, mounting holes 52a-52c and 54a-54c can be threaded, and leverage member adjusters 56 and 58 can be used to manipulate vertebra 70 via the threaded interactions between threaded rod 53 and mounting holes 52a-52c and between threaded rod 61 and mounting holes 54a-54c. In an alternative embodiment, mounting holes 52a-52c and/or 54a-54c may be replaced by one or more continuous grooves in mounting bracket 50. Alternatively, any other configuration(s) may be used.

Mounting bracket 50 can be adjustably mounted to arm 45 via a mounting bracket adjuster 48 and mounting holes 42a-42d. In alternative embodiments, additional or fewer mounting holes may be provided. Mounting bracket adjuster 48 can include a threaded rod configured to mate with a threaded coupling of mounting bracket 50. Mounting holes 42a-42d may also be threaded. Alternatively, any other configuration may be used to secure mounting bracket 50 to arm 45. Mounting bracket adjuster 48 can be used to raise and lower mounting bracket 50 relative to the patient. Mounting holes 42a-42d can be used to hold vertebra 70 in a manipulated position corresponding to movement of vertebra 70 in a direction that is parallel to the top surface of the surgical table and perpendicular to the spinal column of the patient when the patient is lying on the surgical table (i.e., side-to-side translation of vertebra 70 relative to the patient's body). Mounting holes 42a-42d can also be used to hold vertebra 70 in a rotated position in which vertebra 70 is rotated about an axis that is substantially parallel to the spinal column of the patient. Mounting bracket adjuster 48 can also be used to rotate mounting bracket 50 about an axis which is substantially perpendicular to both the top surface of the surgical table and the spinal column of the patient when the patient is lying on the surgical table. In one embodiment, mounting holes 42a-42d may be replaced by one or more grooves.

Arm 45 is mounted to upright 30 by a hinge 40. Hinge 40 can allow arm 45 to be selectively positioned over a working surface such as the surgical table. Hinge 40 can also allow arm 45 to be pivoted away from the surgical table when not in use to provide the surgeon with a clutter-free work area. Upright 30 is mounted to rail 10, and an upright adjuster 20 can be used to secure upright 30 to rail 10 at a desired position along rail 10. In one embodiment, upright adjuster 20 can be threaded into upright 30. A user can tighten upright adjuster 20 to apply pressure to rail 10 such that upright 30 is secured. The user can loosen upright adjuster 20 such that upright 30 can be slid along rail 10 to a desired position. Upright 30 can also be slid along rail 10 to manipulate vertebra 70 along an axis that is parallel to the spinal column (i.e., up and down manipulation relative to the patient).

In one embodiment, a plurality of mounting systems, including uprights and corresponding arms and mounting brackets, can be mounted to rail 10. As such, each individual mounting system can be used to secure one or more manipulated vertebrae. As a result, the surgeon can perform the surgery by his/herself, thereby lowering costs and decreasing risk to the patient. Once the vertebrae have been manipulated and are held in place, the surgeon can mount a stabilizing rod to the vertebrae. The stabilizing rod can be mounted according to any method known to those of skill in the art. For example, looped mounting brackets with set screws can be attached to the vertebrae. The stabilizing rod can be inserted through the mounting brackets and the set screws can hold the stabilizing rod in place. Alternatively, any other method can be used to mount the stabilizing rod to the vertebrae. Once the stabilizing rod is mounted to the patient, the patient can be disengaged from fixation-based surgical system 2, and the surgery can be completed.

In an illustrative embodiment, rail 10 may be permanently or removably mounted to a support (not shown). The support can be a surgical table or other surgical surface. Alternatively, the support can be a wall, a ceiling, a floor, a portable cart, etc. In another alternative embodiment, fixation-based surgical system 2 may not include rail 10. In such an embodiment, upright 30 or arm 45 may be directly mounted to a support such as a wall, a table, a floor, a cart, etc. In one embodiment, a rail and/or corresponding uprights, arms, mounting brackets, etc. may be provided on each side of the patient. In such an embodiment, the rails on each side of the patient can be substantially parallel to one another. In another illustrative embodiment, fixation-based surgical system 2 can be constructed out of a carbon fiber material or other radio-lucent material such that X-rays and other types of imaging may be performed without adversely affecting the resulting images. In alternative embodiments, fixation-based surgical system 2 may be constructed out of any other suitable material such as steel, aluminum, plastic, etc.

Figure 2:
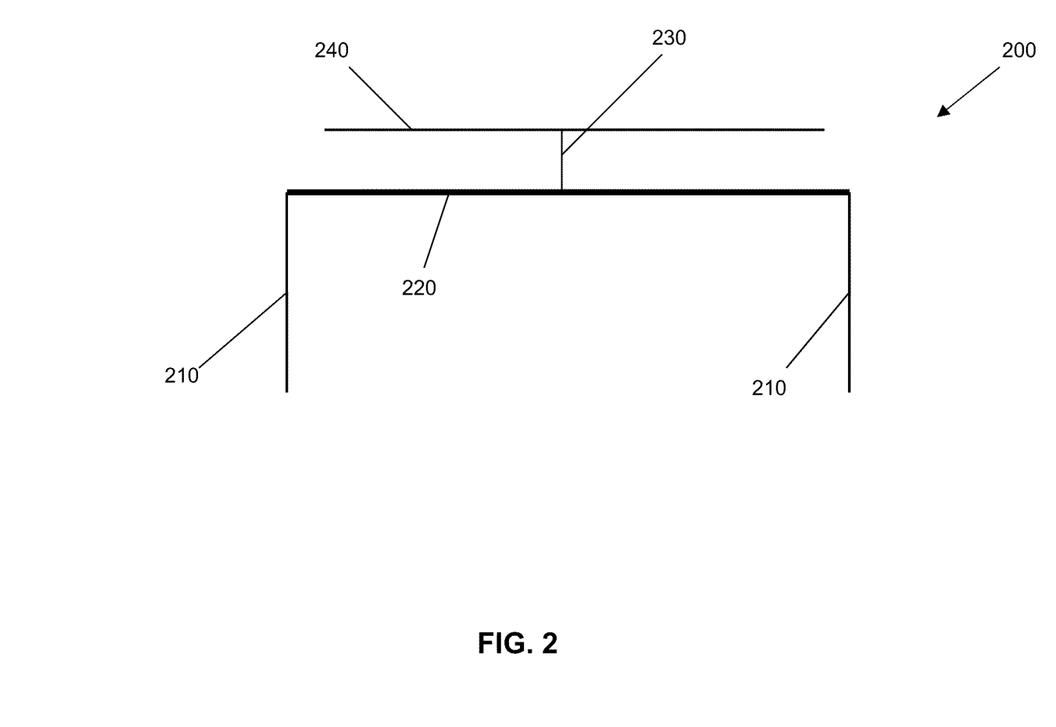
FIG. 2 is a side elevation view of a table of a fixation-based surgical system in accordance with an illustrative embodiment.
Figure 3:
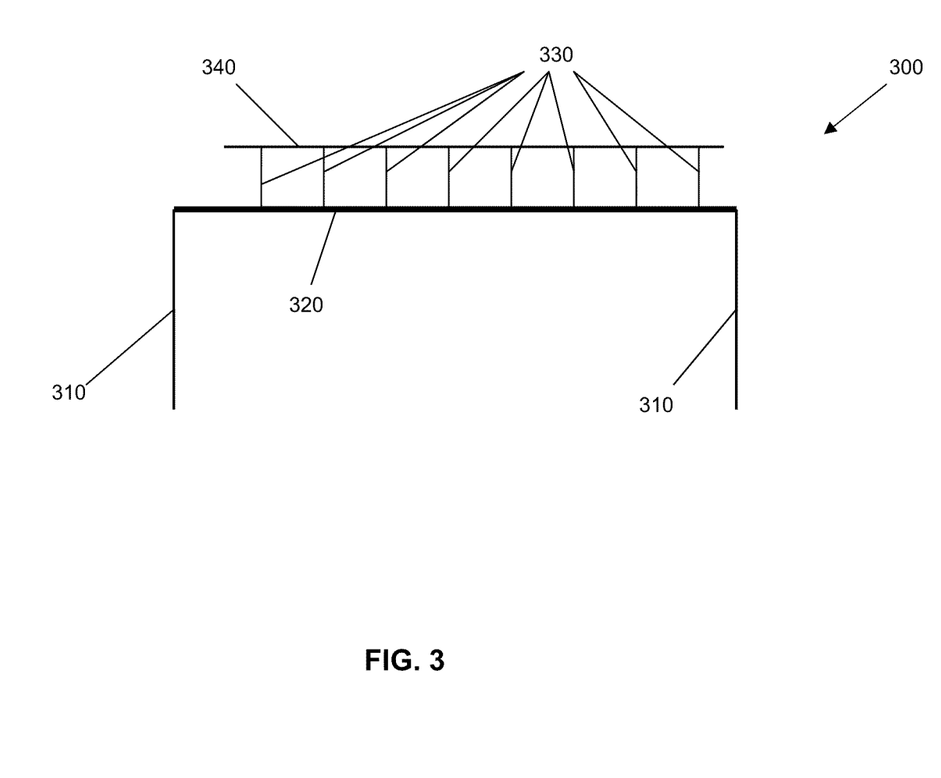
FIG. 3 is a side elevation view of a table of a fixation-based surgical system in accordance with an illustrative embodiment.
Figure 4:
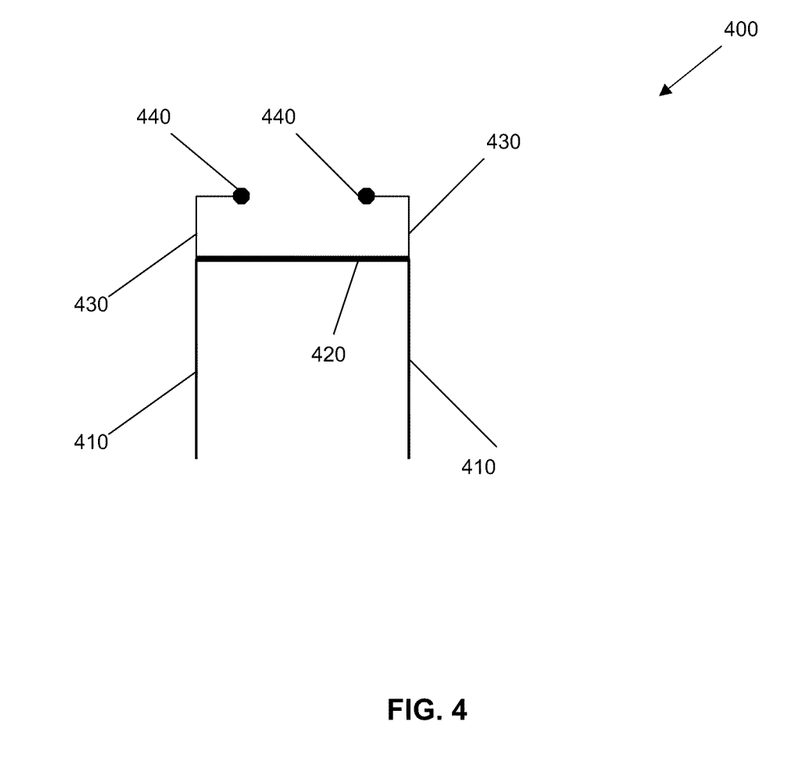
FIG. 4 is an end elevation view of a table of a fixation-based surgical system in accordance with an illustrative embodiment.

FIGS. 2-4 illustrate various embodiments of fixation-based surgical systems mounted to a surface. FIG. 2 is a side elevation view of a table 200 of a fixation-based surgical system in accordance with an illustrative embodiment. Table 200 includes a table top 220 supported by table legs 210. Table 200 also includes a support bar 230 to which a rail 240 is attached. In alternative embodiments, additional support bars may be used. In one embodiment, rail 240 may correspond to rail 10 described with reference to FIG. 1. In such an embodiment, rail 240 can be configured to receive an upright which is mounted to an arm, a mounting bracket, and one or more leverage members. Alternatively, rail 240 may include a plurality of spaced and/or movable mounting brackets which are configured to directly receive and hold leverage members that are mounted to one or more vertebrae. In one embodiment, a rail may be provided on each side of table 200.

FIG. 3 is a side elevation view of a table 300 of a fixation-based surgical system in accordance with an illustrative embodiment. Table 300 includes a table top 320 supported by table legs 310. Table 300 includes a plurality of support bars 330 and a rail 340. In one embodiment, rail 340 may correspond to rail 10 described with reference to FIG. 1. In such an embodiment, rail 340 can be configured to receive an upright which is mounted to an arm, a mounting bracket, and one or more leverage members. Alternatively, rail 340 and/or support bars 330 may include a plurality of spaced and/or movable mounting brackets which are configured to directly receive and hold leverage members that are mounted to one or more vertebrae. In one embodiment, a rail may be provided on each side of table 300.

FIG. 4 is an end elevation view of a table 400 of a fixation-based surgical system in accordance with an illustrative embodiment. Table 400 includes a table top 420 supported by table legs 410. Table 400 also includes support bars 430 and rails 440. Support bars 430 may include one or more support bars connecting each of rails 440 to table top 420. Support bars 430 each include a first portion that is substantially perpendicular to table top 420 and a second portion that is substantially parallel to table top 420. Rails 440 are secured to ends of the second portions of support bars 430 such that rails 440 can be closely positioned to a patient (not shown) lying on table top 420. In an alternative embodiment, support bars 430 may only include the first portions substantially perpendicular to table top 420, and rails 440 may be mounted to the first portions. Rails 440 can be similar to rail 240 described with reference to FIG. 2 and/or rail 340 described with reference to FIG. 3. In an alternative embodiment, only a single rail and single support bar may be used.

Figure 5:
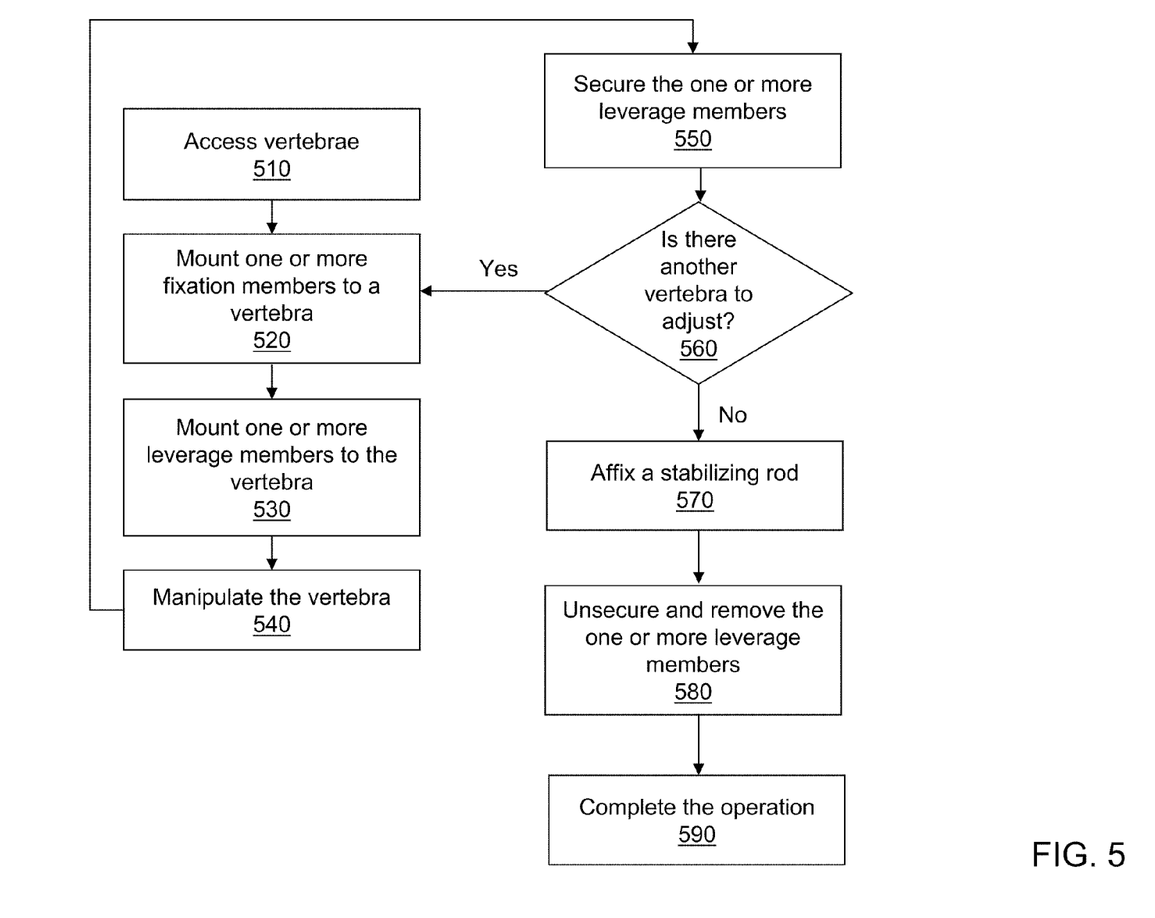
FIG. 5 is a flow diagram depicting operations performed during fixation-based surgery in accordance with an illustrative embodiment.
Figure 6:
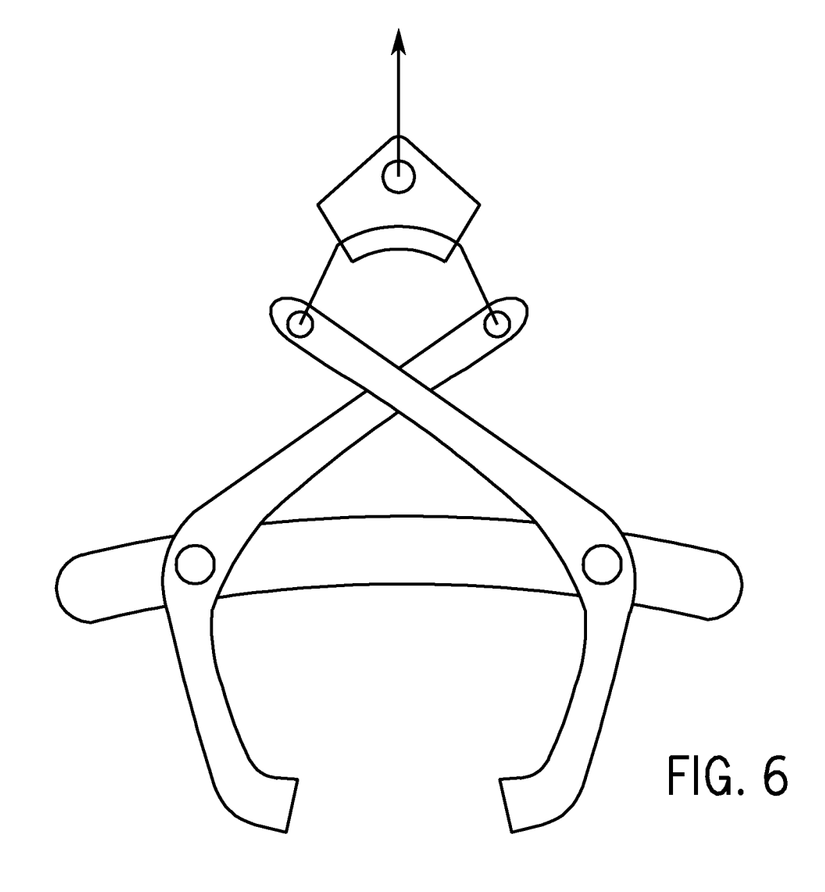
FIGS. 6-8 illustrate components of the system fixation-based surgical system in accordance with an illustrative embodiment.
Figure 7:
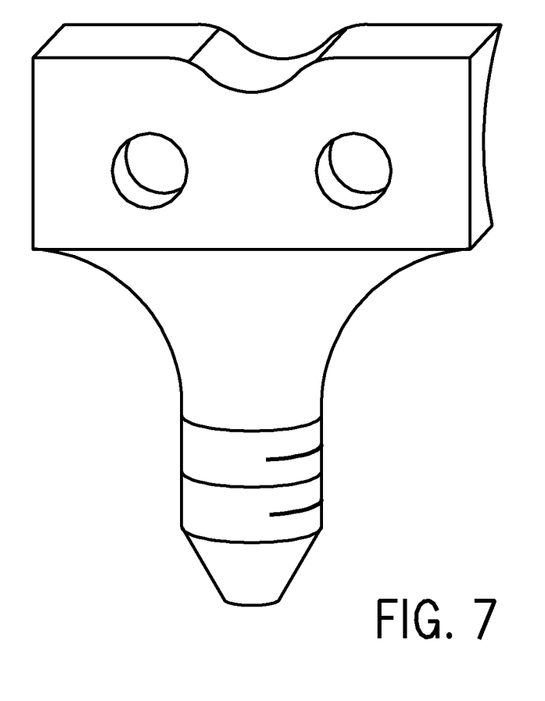
Figure 8:
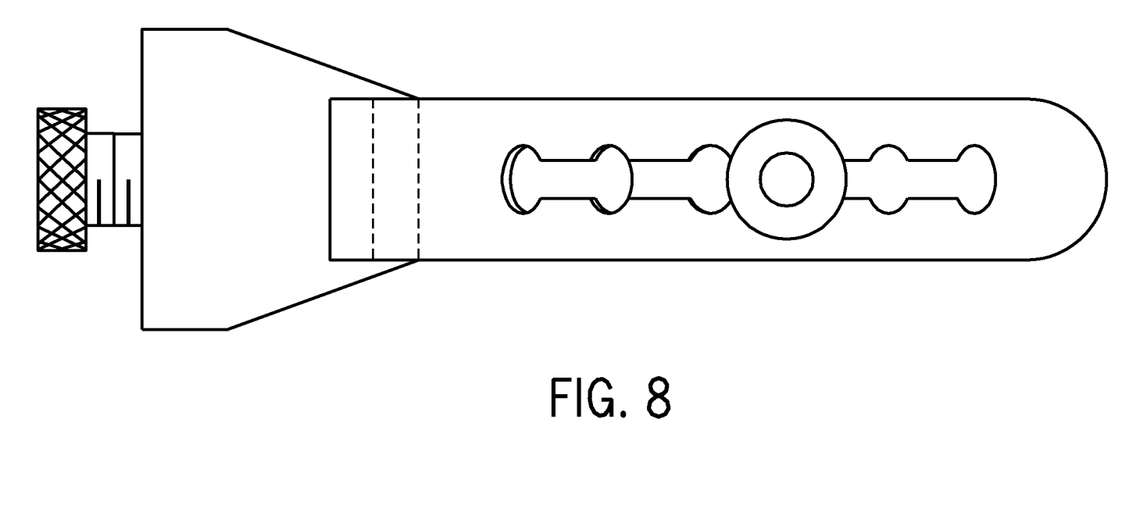

FIG. 5 is a flow diagram depicting operations performed during fixation-based surgery in accordance with an illustrative embodiment. In alternative embodiments, fewer, additional, and/or different operations may be performed. Further, the use of a flow diagram is not meant to be limiting with respect to the order of the operations performed. In an operation 510, one or more vertebrae are accessed by a surgeon. The one or more vertebrae can also be prepped for surgery as known to those of skill in the art. In one embodiment, the surgeon can use X-ray or other image assistance to plan an incision such that the problematic vertebra(e) can be accessed. Once the incision is made, the surgeon can use a retroperitoneal approach to achieve access to the problematic vertebra(e). The surgeon can also mobilize and protect local vasculature on or near the side of the vertebral bodies upon which surgery is performed. Alternatively, any other methods or procedures may be used.

In an operation 520, the surgeon mounts one or more fixation members to a vertebra to be manipulated. In an illustrative embodiment, two fixation members can be used. Alternatively, one, three, four, or any other number of fixation members can be mounted. The surgeon can mount the fixation members into a vertebral body of the vertebra by any method known to those of skill in the art. For example, the surgeon can use a handheld screwdriver, a drill, a mallet, or any other tool capable of inserting the fixation members. The surgeon can also tap or drill pilot holes into the vertebral body prior to inserting the fixation members to help prevent bone fracture. In an illustrative embodiment, the fixation members can be placed with the assistance of fluoroscopy and may be either uni-cortical or bi-cortical in purchase. In one embodiment, the fixation members can be placed bi-cortically into the sacral ala to maximize purchase. The fixation members may include any suitable fasteners known in the art, such as bone screws, anchors, dowels, etc. In one embodiment, the fixation members can be poly-axial screws as known to those of skill in the art.

In an operation 530, one or more leverage members are mounted to the vertebra. In an illustrative embodiment, one leverage member can be mounted to each of the one or more fixation members mounted to the vertebra. Alternatively, any other number of leverage members may be used and/or the leverage members may be mounted using any other method. In one embodiment, the surgeon can mount the one or more leverage members by screwing them onto/into the one or more fixation members via threads. In such an embodiment, the one or more fixation members can have threaded stems configured to receive a threaded portion of the one or more leverage members. Alternatively, the leverage members may be mounted using bolts and/or nuts, a mating connector, and/or any other method.

In an operation 540, the surgeon manipulates the vertebra. The surgeon may manipulate only problem vertebrae, every vertebrae, every other vertebrae, vertebrae which are adjacent to problem vertebrae, and/or any other combination of vertebrae depending on the patient and the deformity to be corrected. Manipulation can include de-rotation of the vertebra in any direction. For example, the surgeon can rotate the vertebra about an axis that runs substantially parallel to the spinal column of the patient. Manipulation can also include a frontward or backward adjustment of the vertebra relative to the patient (i.e., along an axis that is substantially perpendicular to both a top surface of the surgical table and the spinal column of the patient when the patient is lying on the surgical table). Manipulation can also include side-to-side adjustment of the vertebra relative to the patient (i.e., along an axis that is substantially parallel to the top surface of the surgical table and that is substantially perpendicular to the spinal column of the patient when the patient is lying on the surgical table). Manipulation can further include up and down adjustment of the vertebra relative to the patient (i.e., along an axis that is substantially parallel to both the top surface of the surgical table and the spinal column of the patient when the patient is lying on the surgical table). In one embodiment, manipulation can also include rotation of the vertebra about an axis that is substantially perpendicular to the spinal column of the patient. Any other vertebral manipulations may also be performed.

In an operation 550, the one or more leverage members are secured such that the manipulated position of the vertebra can be maintained. In an illustrative embodiment, the one or more leverage members can be secured (or mounted) to any of the illustrative fixation-based surgical systems described with reference to FIGS. 1-4. In another illustrative embodiment, the fixation-based surgical system can include a plurality of different mounting options such that the one or more leverage members can be secured at any position and/or any angle desired by the surgeon. In one embodiment, the surgeon may use the fixation-based surgical system to manipulate the vertebra. In such an embodiment, the surgeon can mount the one or more leverage members to the fixation-based surgical system prior to fully manipulating the vertebra. The surgeon can use adjustment features of the fixation-based surgical system to manipulate the vertebra. Alternatively, the manipulation may be fully performed prior to mounting the one or more leverage members to the fixation-based surgical system.

In an operation 560, the surgeon determines whether there is another vertebra to adjust. If there is another vertebra to adjust, operations 520-550 can be repeated for each additional vertebra to be manipulated. If there is not another vertebra to adjust, the surgeon affixes a stabilizing rod in an operation 570. In one embodiment, the stabilizing rod can be affixed to connectors mounted to the one or more fixation members. For example, each of the one or more fixation members may include a loop configured to receive the stabilizing rod. A set screw in each loop can be used to keep the stabilizing rod from moving. Alternatively, the stabilizing rod can be mounted and secured according to any other methods known to those of skill in the art. In an operation 580, the surgeon un-secures and removes the one or more leverage members from each of the vertebrae. In an operation 590, the surgeon completes the operation. Completion of the operation can include cleaning the patient, closing the incision, and/or any other actions known to those of skill in the art.

For the purposes of this disclosure and unless otherwise specified, "a" or "an" means "one or more." The foregoing description of exemplary embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A stabilization system comprising:
   at least two leverage members configured to be mounted to a single vertebra, and further configured to allow a user to manipulate the vertebra in a direction which is substantially perpendicular to a top surface of a surgical table to a desired position; and
   a mounting bracket configured to mount to the at least two leverage members such that the at least two leverage members are immobilized relative to a fixed point in space, wherein the mounting bracket is mounted to a support, and wherein the mounting bracket comprises a plurality of holes configured to receive the at least two leverage members and to secure the at least two leverage members at a plurality of distinct angles relative to one another;
   wherein the support comprises an arm that includes one or more mounting holes, wherein the mounting bracket is mounted to the support by a mounting bracket adjuster that is configured for insertion into one of the one or more mounting holes, and wherein the mounting bracket adjuster is configured to mount the mounting bracket to the arm via the one or more mounting holes in the arm, and wherein the one or more mounting holes are configured to allow the user to manipulate the vertebra in a direction which is parallel to the top surface of the surgical table and perpendicular to a spinal column comprising the single vertebra.

2. The stabilization system of claim 1, wherein the support comprises a rail, and further wherein the rail is mounted to a surgical table.

3. The stabilization system of claim 2, wherein the mounting bracket is configured for selective movement along the rail.

4. The stabilization system of claim 1, wherein the at least two leverage members comprise at least six degrees of freedom of movement.

5. The stabilization system of claim 4, wherein the six degrees of freedom of movement comprise movement in a medial direction, movement in a lateral direction, movement in a ventral direction, movement in a dorsal direction, and two-way rotation about an axis which runs through the vertebra.

6. The stabilization system of claim 4, wherein the mounting bracket is configured to immobilize the at least two leverage members in each of the at least six degrees of freedom relative to the fixed point in space.

7. The stabilization system of claim 1, wherein the support comprises the arm mounted to an upright via a hinge.

8. The stabilization system of claim 7, wherein the arm is configured for selective positioning of the mounting bracket over the vertebra.

9. The stabilization system of claim 1, further comprising a mounting portion configured to mount to a fixation member that is mounted to the vertebra, wherein the mounting portion is configured for selective connection to the at least two leverage members.

10. The stabilization system of claim 1, wherein the mounting bracket adjuster is configured to rotate the mounting bracket around an axis that is substantially perpendicular to the spinal column.

11. The stabilization system of claim 1, wherein the support is directly mounted to a wall, a table, a floor, or a cart.

12. The stabilization system of claim 1, wherein at least one of the at least two leverage members, the mounting bracket, or the support comprise a radio-lucent material.

13. The stabilization system of claim 1, wherein the support is configured to receive at least two mounting brackets.

14. The stabilization system of claim 13, wherein each of the at least two mounting brackets is configured to mount to two or more leverage members; and
the two or more leverage members of different mounting brackets are configured to be mounted to different vertebrae.

15. The stabilization system of claim 14, wherein the different vertebrae are adjacent to each other.

16. The stabilization system of claim 1, wherein the fixed point in space comprises one of a surgical table, a wall, a ceiling, and a floor.

17. The stabilization system of claim 1, wherein each of the two leverage members comprises a threaded rod, and wherein the manipulation of the vertebra in the direction which is substantially perpendicular to the top surface of the surgical table is by rotating the threaded rod of at least one of the at least two leverage members.

18. The stabilization system of claim 1, wherein the direction which is substantially perpendicular to the top surface of the surgical table comprises a direction which is substantially away from the surgical table.

19. A method comprising:
mounting at least two fixation members to a single vertebra;
mounting a leverage member to each of the at least two fixation members, wherein each of the leverage members comprises a threaded rod;
manipulating the vertebra in a direction which is substantially perpendicular to a top surface of a surgical table by rotating the threaded rod of at least one of the at least two leverage members to a desired position and by adjusting a mounting bracket adjustor of a mounting bracket;
securing the at least two leverage members to holes within the mounting bracket of a stabilization system such that the vertebra is maintained in the desired position relative to a fixed point in space, and such that the at least two leverage members are mounted relative to one another at one of a plurality of distinct angles;
securing the mounting bracket to an arm of the stabilization system via the mounting bracket adjustor, wherein the mounting bracket is mounted to a support, wherein the support comprises the arm, the arm including one or more mounting holes, wherein the mounting bracket is mounted to the support by the mounting bracket adjuster that is configured for insertion into one of the one or more mounting holes, and wherein the mounting bracket adjuster is configured to mount the mounting bracket to the arm via the one or more mounting holes in the arm, and wherein the one or more mounting holes are configured to allow the user to manipulate the vertebra in a direction which is substantially parallel to the top surface of the surgical table and perpendicular to a spinal column comprising the single vertebra;
mounting a stabilizing rod to the vertebra such that the vertebra is maintained in the desired position; and
removing the at least two leverage members.

20. The method of claim 19, wherein said mounting the stabilizing rod to the vertebra comprises affixing the stabilizing rod to at least one of the at least two fixation members.

* * * * *